United States Patent [19]

Berlin et al.

[11] Patent Number: 4,833,254
[45] Date of Patent: May 23, 1989

[54] HETEROAROTINOIDS AS ANTICANCER AGENTS

[75] Inventors: Kenneth D. Berlin; Warren T. Ford; Shirish N. Rajadhyaksha; Jonathan B. Gale; Lyle W. Spruce, all of Stillwater, Okla.

[73] Assignee: The Board of Regents for the Oklahoma Agricultural and Mechanical Colleges acting for and on behalf of Oklahoma State University, Okla.

[21] Appl. No.: 48,586

[22] Filed: May 11, 1987

[51] Int. Cl.⁴ .................. C07D 405/10; C07D 335/06; C07D 311/58
[52] U.S. Cl. ...................... 548/454; 549/398; 549/23
[58] Field of Search .................. 549/398, 23; 548/454

[56] References Cited

U.S. PATENT DOCUMENTS 3,984,440 10/1976 Bollag et al. .................. 549/398
4,678,793 7/1987 Klaus et al. .................. 549/398

Primary Examiner—Nicky Chan
Attorney, Agent, or Firm—Head & Johnson

[57] ABSTRACT

Novel heteroarotinoid compositions characterized by the formulae:

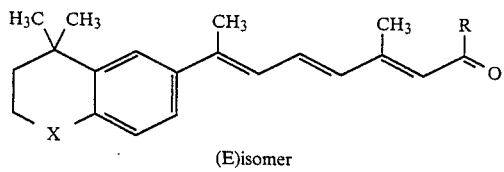

(E)isomer

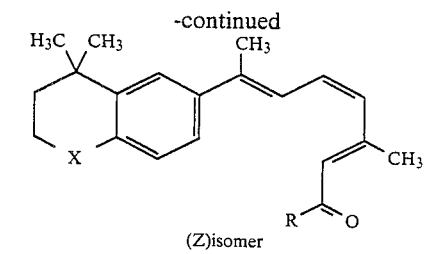
(Z)isomer

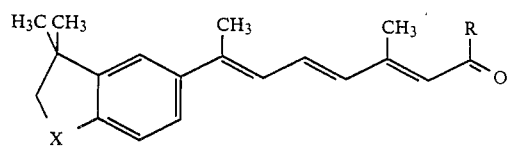
(E)isomer (Z)isomer (E)isomer (Abstract continued on next page.)

-continued
(Z)isomer
where: X is S or O; OAc is the acetate group
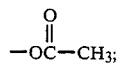
and R is —H, —OH, —OCH$_3$, or —OC$_2$H$_5$ and includes
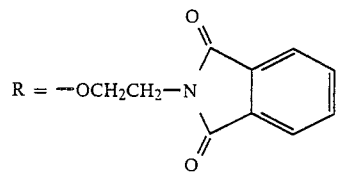
for formulae (1) and (2). Such compositions exhibit activity as anticancer agents.
9 Claims, 1 Drawing Sheet

HETEROAROTINOIDS AS ANTICANCER AGENTS

BACKGROUND OF THE INVENTION

1. Field of the Invention:

This invention relates to anticancer compositions. More specifically, the invention relates to certain novel heteroarotinoids and derivatives thereof.

2. Description of the Prior Art:

Retinoids (vitamin A and derivatives thereof) constitute a group of compounds of enormous current interest. The stimulus for this interest arises from observations that these compounds exhibit some antitumor activity and exert a preventive activity in models of chemical carcinogensis. Unfortunately, the use of natural retinoids in cancer chemotherapy has some disadvantages. With the exception of trans-retinoic acid, natural retinoids are stored in the liver, and blood levels of the materials do not increase proportionately even after massive doses. Thus, it is difficult to achieve a good distribution and to deliver a retinoid to specific target sites. In addition, acute toxicity has been associated with high dosages of natural retinoids. This "hypervitaminosis A" limits clinical use of such compounds. Modifications of the basic retinoid structure have been the subject of intensive effort recently.

For example, systems with fused aryl rings have shown good potency in a tracheal assay. Such systems have been referred to as arotinoids and several papers on the subject have been published, such as in the *European Journal of Medicinal Chemistry*, 1980, Vol. 15, pages 9-15, entitled "Arotinoids, A New Class of Highly Active Retinoids" by P. Loeliger, W. Bollag and H. Mayer. Synthesis and stereochemistry are discussed. A second more recent publication has peripherally related derivatives and is entitled "Fluorinated Retinoic Acids and Their Analogues". Synthesis and Biological Activity of Aromatic 6-Fluoro Analogues" by A. J. Lovey and B. A. Pawson. The article appeared in the *Journal of Medicinal Chemistry, Vol.* 25, pages 71-75 (1982). A review of the entire area of biological activity of retinoids and related compounds has been published in the *Journal of Medicinal Chemistry, Vol.* 25, pages 1269-1277 (1982). The title is "Retinoids at the Threshold: Their Biological Significance and Therapeutic Potential", by B. A. Pawson, C. W. Ehmann, L. M. Itri, and M. I. Sherman. The first paper contains work which is the most closely related to the compounds cited in this application in terms of preparation from ketones and conversion to the final product through a type of Wittig reaction. However, very few publications involving a heteroatom in the ring systems can be currently found and it is felt that the presence of the heteroatom makes a significant difference in the properties of the heteroarotinoids as compared to the arotinoids.

According to the existing literature, some derivatives of the arotinoids have been found to posses useful biological activities. One type of test for therapeutic potency is the antipapilloma test (cited in the first article above) and the tracheal organ culture assay which is described in an article in the *Journal of Cancer Research, Vol.* 40, 3413-3425 (1980) by D. L. Newton, W. R. Henderson, and M. B. Sporn. The assays assess the ability of the test compound to prevent skin papillomas and carcinomas in mice or to prevent keratinization of cultured tracheal cells which frequently occurs when cells become premalignant. Further evidence on these points can be found in articles entitled "Chemoprevention of Cancer with Retinoids" by M. B. Sporn and D. L. Newton, published in the *Federation Processings, Vol.* 38, pages 2528-2534 (1979) and "Structure-Activity Relationships of Retinoids in Hamster Tracheal organ Culture" by D. L. Newton, W. R. Henderson, and M. B. Sporn, published in *Cancer Research*, Vol. 40, pages 3414-3425 1980). Another test for potential anticancer activity of retinoic acid derivatives has been the ornithine decarboxylase assay which has been reviewed recently in connection with an evaluation of some aromatic retinoic acid compounds. The article is entitled "Aromatic Retinoic Acid Analogues. Synthesis and Pharmacological Activity" by M. I. Dawson, R. Chan, P. D. Hobbs, W. Chao, and L. J. Schiff and was published in the *Journal of Medicinal Chemistry*, Vol. 26, pages 1282-1293 (1983). The compounds of the present inventions were assayed using the tracheal organ culture procedure as well as assayed for the induction of differentiation of human (HL-60) promyelocytic cells.

In an article by Waugh et al. "Synthesis and Characterization of Selected Heteroarotinoids", *Journal of Medicinal Chemistry*, 1985, 28, 116, a series of heteroarotinoids based on the E isomer of 2-arylsubstituted parapecopenylbenyoates having a 4.4-dimethyl chromanyl-6-yl (or corresponding thiochromanyl or -1-oxothiochromanyl) bicyclic heteroatom containing ring structure as the substituent, the tracheal organ culture assay of selected heteroretinoids are compared with trans-retinoic acid for ability to reverse keratinization in vitamin A deficient hamsters. In an article by Dawson et al. "Conformationally Restricted Retinoids", *Journal of Medicinal Chemistry*, 1984, 27, 1516, a series of conformationally restricted retinoids was synthesized and acreened in two assays, Keratinization in tracheal organ culture (TOC) from vitamin A deficient hamsters and the inhibition of the induction of mouse epidermal ornithine decarboxylase (ODC) by a tumor promoter. It was found that the toxicity of these compounds correlated with their activity in the TOC assay and that the heterocyclic analogues tended to be less toxic.

SUMMARY OF THE INVENTION

The present invention involves novel (E) and (Z)-isomers of chroman and thiochroman heterocyclic analogues of retinoic acid and derivatives thereof wherein the 1-position of the tetrahydronapthalene ring has been replaced by oxygen and sulfur, respectively. The presence of both the heteroatom and the bicyclic aryl group are felt to retain the desired activity at reduced toxicity. The invention further involves novel derivatives of the (E) and (Z)-isomers containing chromanyl and thiochromanyl structure wherein the derivative further contain a cyclic ether group representing a synthetic biological metabolite analog of retinoic acid which is felt to further reduce the toxicity.

Thus, the present invention provides novel heteroarotinoids characterized by the formulae:

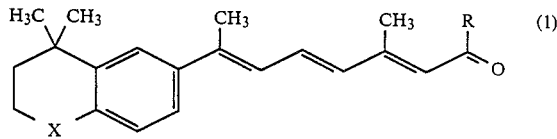

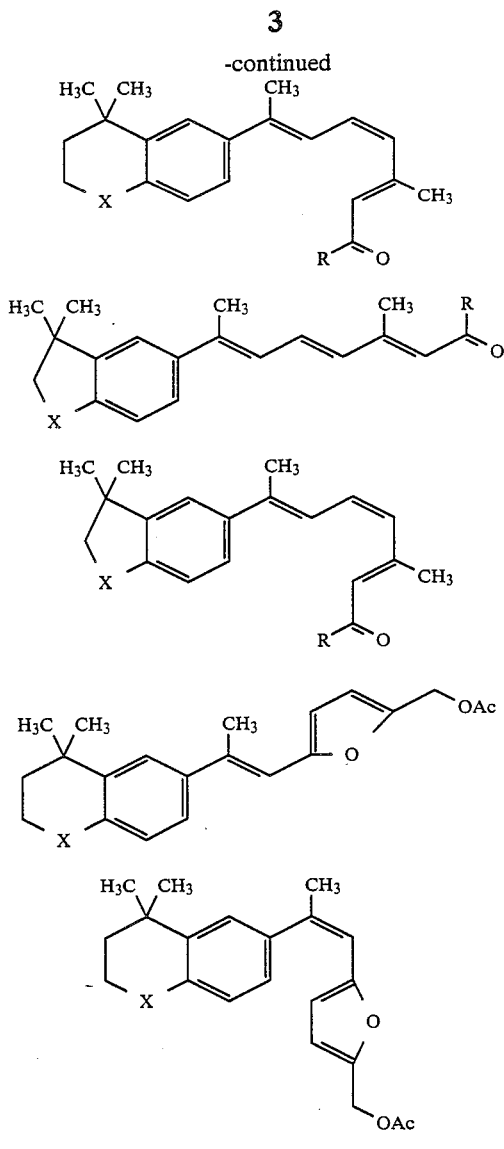

where: X is S or O; OAc is the acetate group

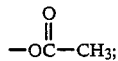

and R is —H, —OH, —O CH₃, or —OC₂H₅ and includes

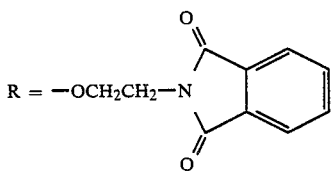

for formulae (1) and (2).

It is an object of the present invention to provide novel heteroarotinoids which are structurally related to trans-retinoic acid and 13-cis-retinoic acid and which act as anticancer agents for the treatment of skin disorders and tumors and display reduced toxicity. Fulfillment of this object and the presence and fulfillment of other objects will be apparent upon complete reading of the specification and claims.

DESCRIPTION OF THE PREFERRED EMBODIMENTS

Figure 1:
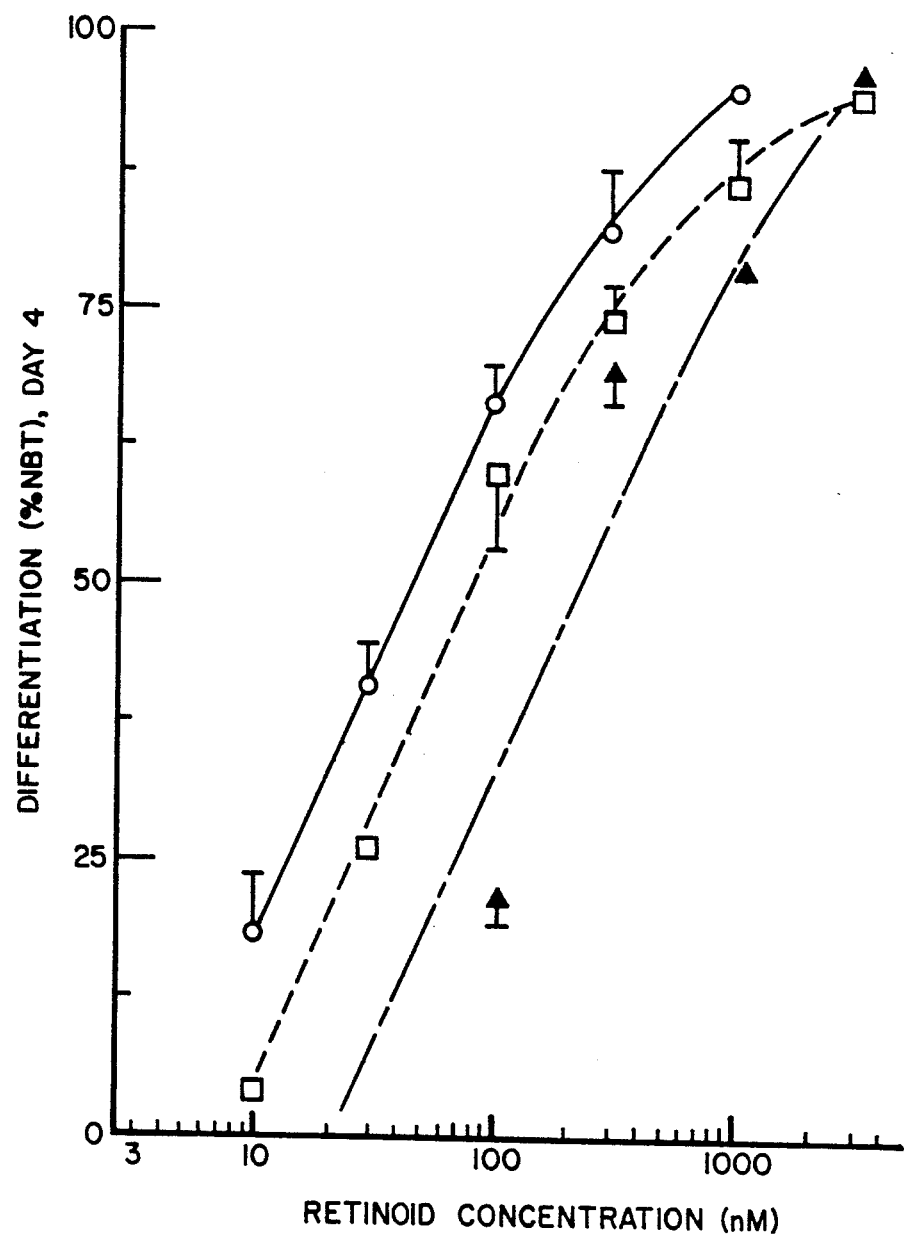
FIG. 1 is a plot of the induction of differentiation of HL-60 cells as a function of retinoid concentration for trans-retinoic acid and two heteroaretinoids according to the present invention.

The novel heteroarotinoid compositions according to the preferred embodiments of the present invention are heteronuclear ring, organic compounds based on the generic structures designated below as compounds (1) through (6). As shown in these structural formulae, the 1-position is occupied by the heteroatom which is either a sulfur or oxygen atom (for purposes of this invention the heteroatom is symbolized by X in the formulae). As structurally illustrated in the formulae the heteroatom appears in the ring portion of the arotionoid while the remaining portion of the structure is extremely reminiscent of the corresponding portion of the retinoid structure (see formulae 1, 2, 3 and 4) or a potential biological metabolite of this portion of the retinoid structure (see formulae 5 and 6). The R in the formulae symbolizes a hydrogen (aldehyde form), methoxyl, ethoxyl or other oxyalkyl and substituted oxyalkyl group (ester form) or hydroxyl group (acid form). The OAc in formulae 5 and 6 represents the acetate group. As exemplified later, the compositions of the present invention exhibit good biological activity with respect to accepted assays such as reversal of keratinization in the tracheal organ culture (TOC), induction of mouse epidermal ornithine decarboxylase (ODC) by a tumor promoter and induction of differentiation of human (HL-60) promyelocytic cells. Furthermore, they appear to be less toxic than the standard retinoids.trans-retinoic acid and 13-cis-retinoic acid.

PRODUCTS

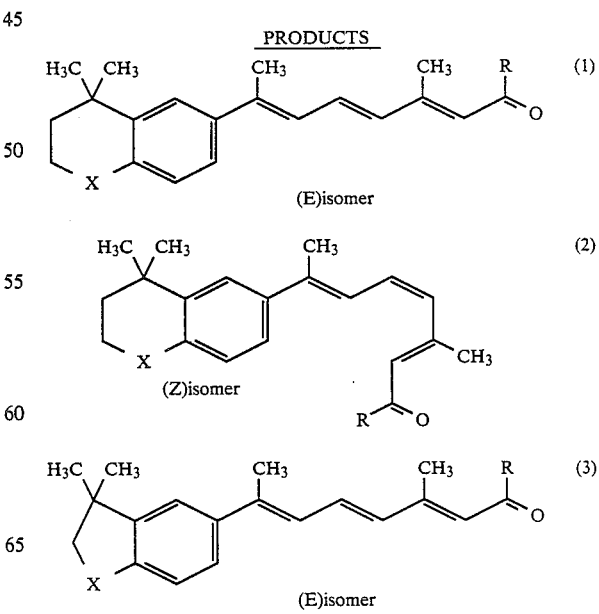

-continued
PRODUCTS

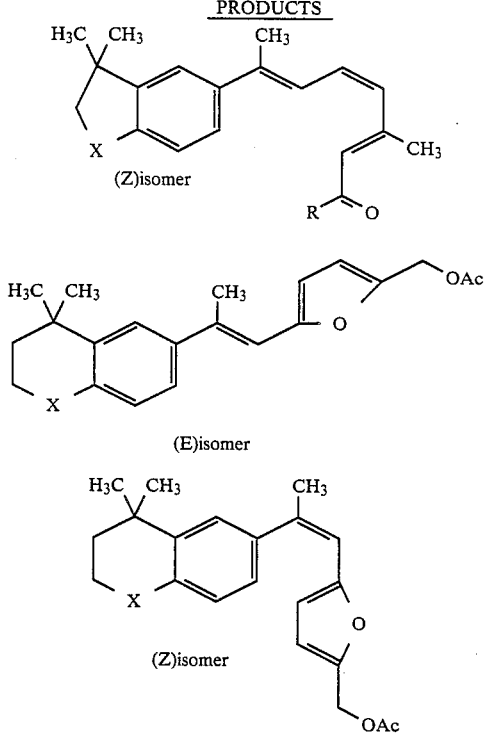

Typically, the compounds according to the present invention are or can be synthesized by one of the following generalized reaction schemes. These schemes involve the synthesis of the known ketones (10) and (27) or alcohol (21); the number in parenthesis as used herein correspond to numerically identified formulae. The ketone or alcohol is then converted to a salt (12), (22), (29) or (30) with triphenylphosphine hydrobromide typically in methanol and subsequently reacted with an aldehyde (e.g., ester-aldehyde) in a reducing environment (e.g., BuLi ether) to produce the heteroarationoid structure (13), (23) or (31). The ester can then be modified to produce other desired derivatives. Various recrystallization and purification steps can be employed to achieve the desired degree of purity of compounds and isomers isolated.

More specifically, reaction scheme A illustrates starting with an ethyl 3-(phenylthio or phenyloxo)propionate (7) and then converting this starting material to the corresponding 2-methyl-4-(phenylthio or phenyloxo)-2-butanol (8) by the action of methylmagnesium iodide. The heteroatom containing ring of the correspond chroman or thiochroman structure (9) is produced by reaction of $P_2O_5$ in sodium-dried benzene. The known ketone structure (10) is produced in the next step by the reaction of acetyl chloride in a $CS_2$ suspension of $AlCl_3$. The ketone (10) is then reacted with vinyl magnesium bromide in tetrahydrofuran producing the vinyl alcohol (11). The corresponding phosphonium salt (12) is synthesized by reacting the vinyl alcohol (11) with triphenylphosphine hydrobromide in methanol. The phosphonium salt (12) reacts in n-butyllithium with ethyl (E)-β-formylcrotonate by several alternate methods to sequential produce the ester form of the heteroarotinoid (13) which is then under control acidity isolated as the acid (14). The acid form can then be further converted to ester derivatives (15) and (16), all as exemplified later.

REACTION SCHEME A

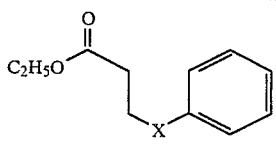 (7)

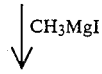

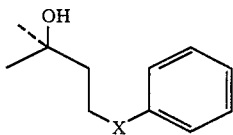 (8)

For (X = O): AlCl₃/CH₃NO₂    For (X = S): H₃PO₄/P₂O₅ C₆H₆

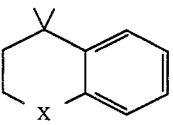 (9)

$$\begin{array}{c} O \\ \parallel \\ CH_3C-Cl \\ AlCl_3/CS_2 \end{array}$$

-continued
REACTION SCHEME A
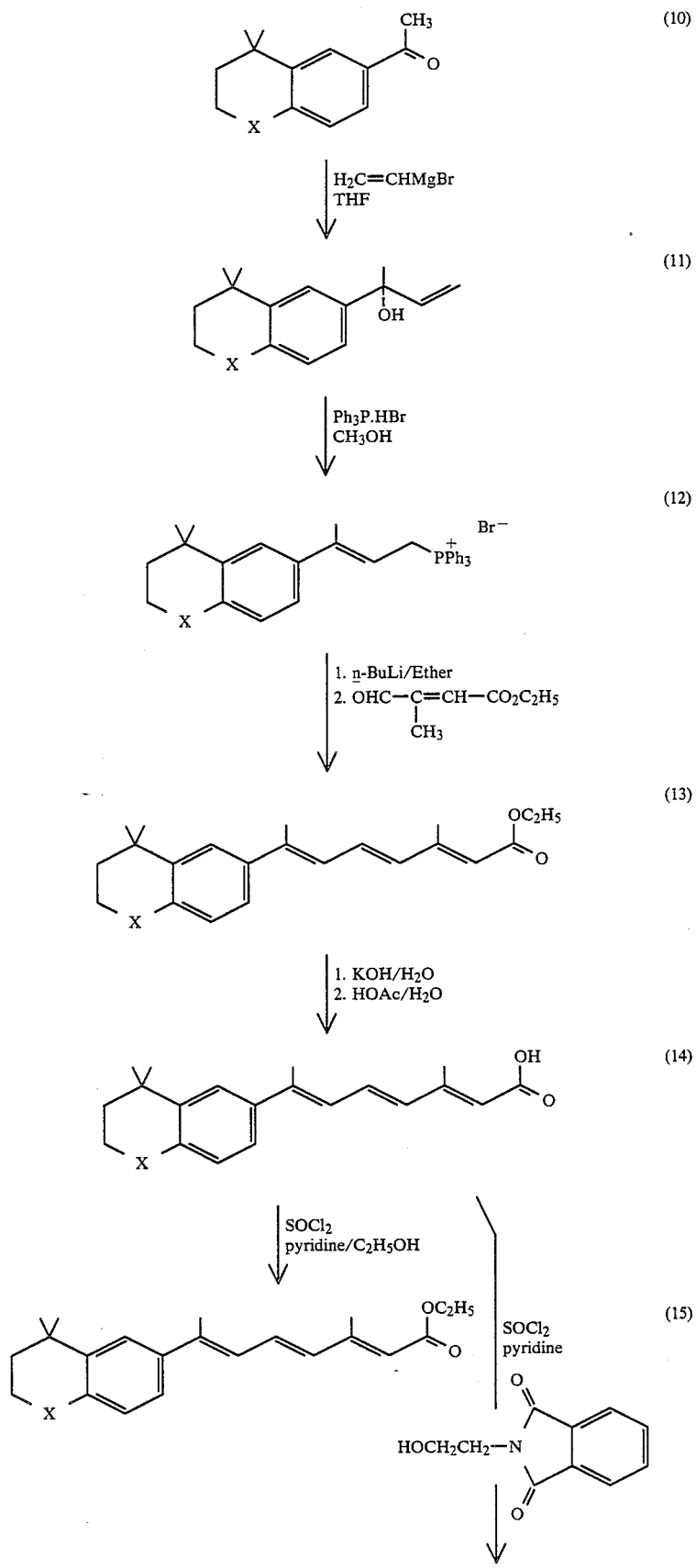

REACTION SCHEME A
-continued

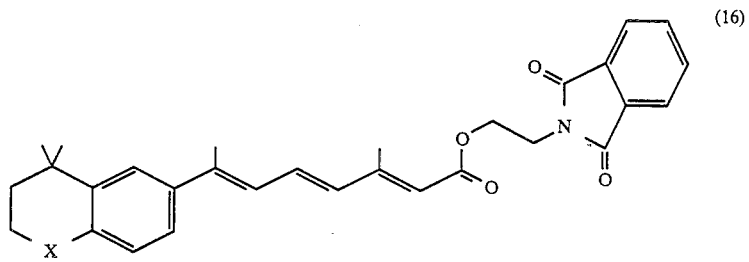

Reaction scheme B is similar to the previously described scheme except a 4-bromanisole (18) or corresponding thioanisole is reacted with β-methallyl chloride (17) in concentrated H₂SO₄ to produce the chlorobutane (19) which is subsequently converted to a five-member heteroatom containing ring. This is accomplished in the second step by the use of pyridine hydrochloride and quinoline with heat producing the bromine substituted dimethybenzofuran and corresponding thiofuran (20). This in turn is converted to the corresponding Grignard reagent by use of Mg in dry THF which is treated with acetaldehyde to give the alcohol (21) reminiscent of the previous formation of ketone (10) followed by vinyl alcohol formation (11). The alcohol (21) is then converted to the corresponding triphenylphosponium bromide salt (22) analogous to the previous compound (12) of reaction scheme A. The triphenylphosphonium bromide salt can then be reacted in the presence of butyllithium and the appropriate unsaturated ester-aldehyde to produce the heteroarotinoid esters (23) of the present invention. Further purification, isolation and conversion to other derivatives can be performed on esters (23) as previously illustrated in scheme A.

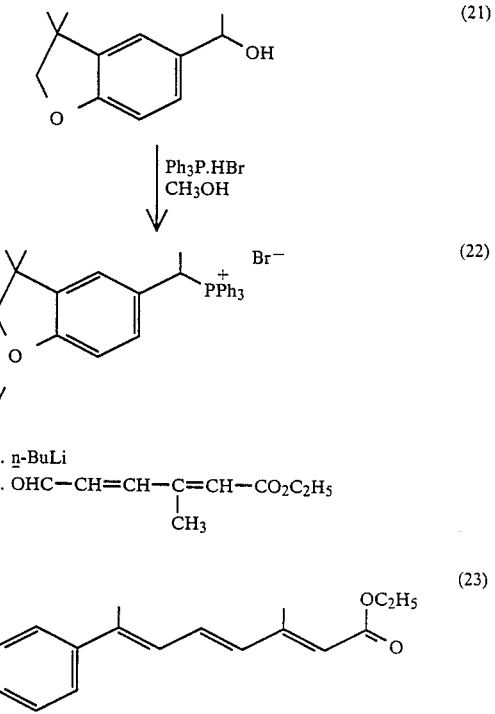

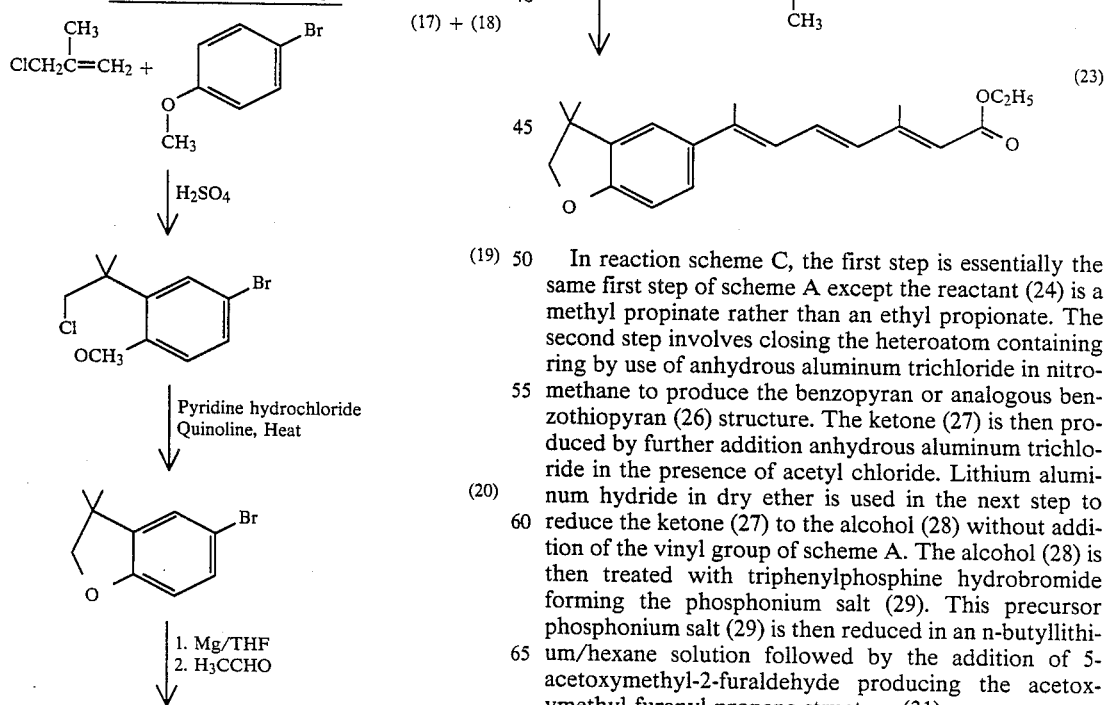

In reaction scheme C, the first step is essentially the same first step of scheme A except the reactant (24) is a methyl propinate rather than an ethyl propionate. The second step involves closing the heteroatom containing ring by use of anhydrous aluminum trichloride in nitromethane to produce the benzopyran or analogous benzothiopyran (26) structure. The ketone (27) is then produced by further addition anhydrous aluminum trichloride in the presence of acetyl chloride. Lithium aluminum hydride in dry ether is used in the next step to reduce the ketone (27) to the alcohol (28) without addition of the vinyl group of scheme A. The alcohol (28) is then treated with triphenylphosphine hydrobromide forming the phosphonium salt (29). This precursor phosphonium salt (29) is then reduced in an n-butyllithium/hexane solution followed by the addition of 5-acetoxymethyl-2-furaldehyde producing the acetoxymethyl furanyl propene structure (31).

REACTION SCHEME C

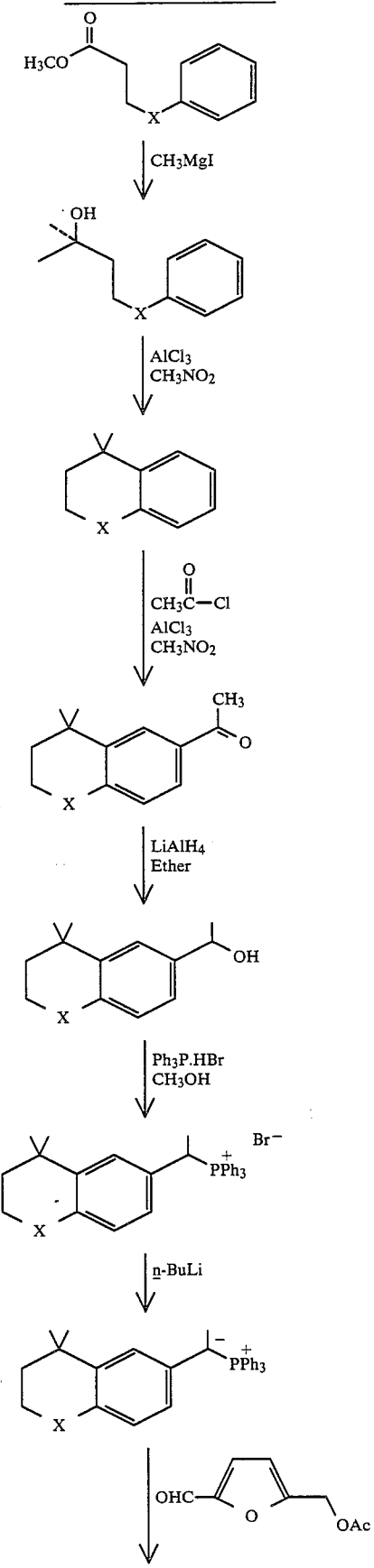

-continued
REACTION SCHEME C

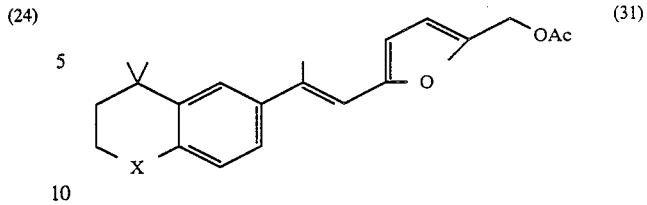

In order to further illustrate the general synthesis of the heteroarotinoids according to the present invention; their respective preparation and isolation as a purified biologically active heterocycle; and their activity in the ornithine decarboxylase assay as well as the HL-60 human leukemic cell line, the following sequence of examples was performed.

EXAMPLES

Preparation of Ethyl 3-(Phenylthio)Propionate (32)

To a solution of 12.12 g (0.11 mol) of thiophenol, 10.01 g(0.10 mol) ethyl acrylate, 20 mL of HCCl$_3$ at 0° C. in a 100-mL, round-bottom flask, 0.50 mL of triethylamine was added under N$_2$. The ice bath was removed after the addition of triethylamine and the solution was allowed to stir at room temperature for 3 hours. The resulting solution was idluted with 150 mL of ether and washed with 10% NaOH, H$_2$O, and saturated NaCl solution. The mixture was dried (Na$_2$SO$_4$, overnight) and the solvents were removed. Vacuum distillation gave 19.36 g (92.1%) of ethyl 3-(phenylthio)propionate as a clear, colorless liquid: bp 112°–115° C./0.2 mm [literature reports 117° C. /2.5 mm; see K. Iwai, H. Kosugi, A. Miyazaki, and Huda, *Synthetic Comunications*, 6, 357 (1976)]; IR (neat) 1740 cm$^{-1}$ (C=O); $^1$H NMR (DCCl$_3$) δ1.14 [t, 3 H, CO$_2$CH$_2$CH$_3$], 2.54[t, 2 H, CH$_2$CO$_2$CH$_2$CH$_3$], 3.10[t, 2 H, ArSCH$_2$], 4.06[q, 2 H, CO$_2$CH$_2$CH$_3$], 7.13–7.32[m, 5 H, ArH]; $^{13}$C NMR (DCCl$_3$) ppm 13.6 [CO$_2$CH$_2$CH$_3$], 28.3[ArSCH$_2$], 33.8[CH$_2$CO$_2$CH$_2$CH$_3$], 60.0 [CO$_2$CH$_2$CH$_3$], 125.8, 128.4, 129.3, 134.8, 170.9 [C=O]. Both hydrogen and carbon-13 NMR spectra shifts were measured from tetramethylsilane (TMS) standard on a Varian XL-300 spectrometer confirming the correct hydrogen distribution and carbon atom assignments.

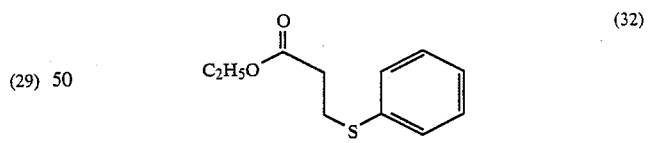

2-Methyl-4(phenylthio)-2-butanol (33)

To a freshly prepared solution of methylmagnesium iodide [42.59 g, (0.30 mol) of methyl iodide, 7.41 grams (0.305 g at) of magnesium]in 75 mL of ether, 21.03 g (0.10 mol) of ethyl 3-(phenylthio)propionate in 25 mL of ether was added dropwise under N$_2$ in a 500-mL, round-bottom flask equipped with a condenser and a nitrogen inlet. The solution was boiled for 1 hour and allowed to stir at room temperature for 10 hours. The resulting solution was neutralized with dilute H$_2$SO$_4$; the ether layer was separated, and the aqueous layer was extracted with ether (3×75 mL). The ether layers were combined and dried (Na$_2$SO$_4$, overnight). Solvent was evaporated and vacuum distillation of the residual oil gave 19.02 g (78.5%) 2-methyl-4-(phenylthio)-2-butanol as a clear colorless liquid: by 106°-107.5° C./0.15 mm [literature reports 110°-113° C./0.17 mm, see F. Montanari, R. Daniel, H. Hogeveen, and G. Maccagnani, *Tetrahedron Letters*, 2685 (1964)]; IR (neat) 3400 cm$^{-1}$ br (OH); $^1$H NMR (DCCl$_3$) δ1.18 [s, 6 H, (CH$_3$)$_2$C], 1.76[m, 2 H, ArSCH$_2$CH$_2$], 2.74 [br s, 1 H, OH] 0.95 [m, 2 H, ArSCH$_2$], 7.10-7.36 [m, 5 H, ArH]; $^{13}$C NMR (DCCl$_3$) ppm 28.6 [ArSCH$_2$CH$_2$], 29.3 [(CH$_3$)$_2$C], 42.7 [ArSCH$_2$CH$_2$], 70.7 [(CH$_3$)$_2$C], 125.9, 128.9, 136.5.

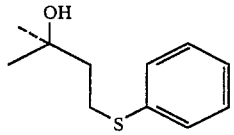

(33)

4,4-Dimethylthiochroman or 3,4-Dihydro-4,4-dimethyl-2H-1 benzothiopyran (34)

A mixture of 15.00 grams (0.076 mol) of 2-methyl-4-(phenylthio)-2-butanol, 12.75 grams of H$_3$PO$_4$, 27.0 grams (0.190 mol) of P$_2$O$_5$ [this is added in three equal portions every 8 h]and 60 mL of sodium-dried benzene was boiled under N$_2$ for 24 hours in a 250-mL, round-bottom flask equipped with a condenser and nitrogen inlet. The resulting, cooled heterogeneous mixture was separated and the P$_2$O$_5$ layer was extracted with ether. The combined organic layers were washed with H$_2$O, brine, dried with Na$_2$SO$_4$ (4 h). Evaporation and vacuum distillation gave 11.68 grams (86.0%) of 4,4-dimethylthiochroman as a clear colorless liquid: bp 75°-82° C./0.1 mm; $_1$H NMR (DCCl$_3$) δ1.29 [s, 6 H, (CH$_3$)$_2$C]1.92 [m, 2 H, ArSCH$_2$CH$_2$]3.00 [m, 2 H, ArSCH$_2$CH$_2$]6.90-7.32 [m, 4 H, Ar-H]; $^{13}$C NMR (DCCl$_3$) ppm 22.8 [ArSCH$_2$CH$_2$], 29.9 [(CH$_3$)$_2$C]32.6 [(CH$_3$)C], 37.4 [ArSCH$_2$CH$_2$], 123.7, 125.7, 126.1, 126.2, 131.5, 141.5.

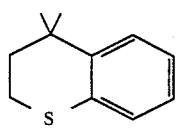

(34)

6-Acetyl-4,4-dimethylthiochroman or 1-(3,4-Dihydro-4,4-dimethyl-2H-1-benzothiopyran-6-yl)ethanone (35)

A solution of 10.0 g (0.056 mol) of 4,4-dimethylthiochroman and 4.4 g (0.056 mol) of acetyl chloride in 150 mL of CS$_2$ was added dropwise over a 45-minutes period to a stirred CS$_2$ suspension of AlCl$_3$ (11.22 g, 0.084 mol) in a 500-mL, round-bottom flask equipped with a condenser and nitrogen inlet. The resulting yellowish-orange mixture was allowed to stir for 10 hours at room temperature; 80 mL of ice water was added and the two layers separated. The aqueous layer was extracted with ether (3×50 mL); the ether layers were combined and dried (Na$_2$SO$_4$, 6 h). After evaporation, the resulting light yellow oil was vacuum distilled to give 10.83 grams (87.6%) of 6-acetyl-4,4-dimethylthiochroman as a yellowish viscous oil: bp 168°-173° C./1.0 mm; IR (neat) 1680 cm$^{-1}$; $^1$H NMR (DCCl$_3$ δ1.31 [s, 6 H, (CH)$_3$)$_2$C], 1.89 [m, 2 H, ArSCH$_2$CH$_2$], 2.52 [s, 3 H, CH$_3$C═O]3.01 [m, 2 H, ArSCH$_2$CH$_2$], 7.11 [d, 1 H, J=8.1 Hz, H(8)], 7.57 [dd, 1 H, J=1.7 Hz, J=8.1 Hz, H(7)], 8.00 [d, 1 H, J=1.7 Hz, H(5)]; $^{13}$C NMR ppm 23.1 [ArSCH$_2$CH$_2$]26.2 [CH$_3$C═O], 29.8 [(CH$_3$)$_2$C], 32.8 [(CH$_3$)$_2$C], 36.8 [ArSCH$_2$CH$_2$], 125.8, 126.2, 132.9, 139.4, 141.7, 196.7 [CH$_3$C═O].

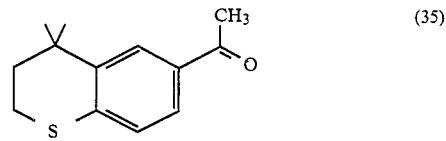

(35)

2-[4,4-Dimethylthiochroman-6-yl]-2-hydroxy-3-butene (36)

To a freshly prepared solution of vinylmagnesium bromide; [7.65 g (0.0715 mol) of vinyl bromide and 1.75 grams (0.0720 g at) of magnesium in 40 mL of dry THF], 10.5 g (0.0477 mol) 6-acetyl-4,4-dimethylthiochroman in 25 mL of THF was added dropwise under N$_2$ in a 200-mL, round-bottom flask equipped with a condenser and nitrogen inlet. The solution was then boiled for 1 hour and allowed to stir for 10 hours at room temperature. Saturated NH$_4$Cl was added in 1-mL portions until the solution was slightly acidic (pH approx. 6.8 ), and 100 mL of ether was added and the two layers separated. The aqueous layer was extracted with ether (4×100 mL) and the ether extracts were combined with the original organic layer. The combined organics were washed with 50 ml of H$_2$O and 50 mL of brine and was then dried (Na$_2$SO$_4$, 4 h). After evaporation, the resulting oil was used without further purification; IR (neat) 3200-3600 cm$^{-1}$ (OH); $^1$H (DCCl$_3$) δ1.32 [s, 6 H, (CH$_3$)$_2$C], 1.95 [m, 2 H, ArSCH$_2$CH$_2$], 2.11 [bs, 1 H, OH], 3.00 [m, 2 H, ArSCH$_2$CH$_2$], 5.14 [dd, 1 H, J=2.0 Hz, J=10.5 Hz, CH═CH$_2$ (cis)], 5.30 [dd, 1 H, J=2.0 Hz, J=15.0 Hz, CH═CH$_2$(trans)], 6.16 [dd, 1 H, J=10.5 Hz, J=15.0 Hz, CH═CH$_2$], 7.05 [d, 1 H, J=8 Hz, H(8)], 7.12 [dd, 1 H, J=Hz, J=8 Hz, H(7)], 7.52 [d, 1 H, J=2 Hz, H(8)]; $^{13}$C (DCCl$_3$) ppm 22.9 [ArSSCH$_2$CH$_2$], 29.1 [CH$_3$COH], 30.2 [(CH$_3$)$_2$C], 33.1 [(CH$_3$)$_2$C], 37.3 [ArSCH$_2$CH$_2$], 74.5 [CH$_3$COH], 112.1, 123.2, 126.2, 130.2, 141.6, 142, 144.7.

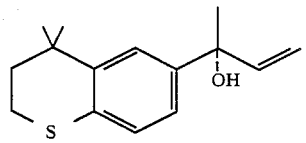

(36)

Phosphonium Salt (37)

To a suspension of 10.78 grams (2.28 mmol) of triphenylphosphine hydrobromide in methanol (20 mL) was added the previously prepared alcohol ( ) in a 100-mL, round bottom flask and stirring was initiated at room temperature and continued for 9.5 hours. Methanol was removed (vacuum) from the clear solution and ether (approx. 50 mL) was added and crystallization occurred within a short time. After standing overnight, 0.91 g (63.0% from the vinyl alcohol) of white crystals were collected, recrystallized (methanol/ether) and dried (vacuum): mp 268.5°-269.5° C. dec; $^1$H NMR (DCCl$_3$) 1.26 [s, 6H, (CH$_3$)$_2$C], 1.63 [d, 3 H, J=4.0 Hz, CH$_3$C═CH], 1.93 [m, 2 H, ArSCH$_2$CH$_2$], 3.02 [m, 2 H, ArSCH$_2$CH$_2$], 4.89 [dd, 2 H, J=8.0 Hz, J=8.0 Hz, J =1.51[J$_{PH}$], C=CHCH$_2$P], 5.6 [tq, 1 H, J=4.0 Hz, J=8.0 Hz, CH$_3$C=CHCH$_2$P], 6.85[dd, 1H, J=2.0 Hz, J =8.1 Hz, H(7)], 7.00 [d, 1 H, J=8.1 Hz, H(8)], 7.17[d, 1 H, J=1.7 Hz, H(5)], 7.66–8.00 [m, 15H, P(ArH)$_3$]; $^{13}$C NMR (DCCl$_3$) ppm 17.0 [CH$_3$C=CH], 23.0 [ArSCH$_2$CH$_2$], 25.4 [d, J=49 Hz [J$_{CP}$], C=CHCH$_2$], 30.1[CH$_3$)$_2$C], 33.0[(CH$_3$)$_2$C], 37.4 [ArSCH$_2$CH$_2$], 110.2 110.3, 117.6, 118.8, 123.4, 123.9, 126.4, 130.2, 130.4, 132.1, 133.9, 134.1, 135.0, 138.0, 138.1, 141.9, 145.4, 145.6; $^{31}$P (DCCl$_3$) ppm 21.6, Anal. Calcd for C$_{33}$H$_{34}$SPBr: C, 69.10; H, 5.98; P, 5.40. Found: C, 69.21; H, 6.07; P, 5.41.

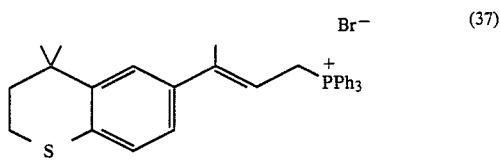

(37)

7-[4.4-Dimethylthiochroman-6-yl]-3,7-dimethyl-2.4,6-heptatrienoic acid (38)

Method 1

To a suspension of 5.82 g (0.01015 mol) of phosphonium salt 37 in mL of ether, was added dropwise n-butyllithium (6.76 mL, 1.50M. 0.010 mol) at room temperature under N$_2$. The resulting, dark read solution was cooled to −78° C., and 1.44 g (0.01015 mol) of ethyl (E)-β-formylcrotonate in 10 mL of ether was added dropwise in the dark. The solution is allowed to warm to room temperature and stir for 24 hours. The resulting organish-yellow suspension was diluted with 25 mL of hexane and filtered. The clear solution was washed with water (2×50 mL), passed through anhydrous Na$_2$SO$_4$ and evaporated (vacuum) to give a yellow oil. The oil was dissolved in 50 mL of absolute ethanol and added to a mixture of 2.3 g KOH in 10 mL of H$_2$O under N$_2$. The new ethanol and added to a mixture of 2.3 g KOH in 10 mL of H$_2$O under N$_2$. The new solution was boiled at reflux for 1 hour and the reddish mixture was allowed to cool to room temperature. The solution was acidified with 50% acetic acid which formed a yellow suspension after extraction with ether (3×100 mL) and evaporation (vacuum) gave a yellow solid. The solid was fractionally recrystallized (absolute ethanol) and dried under high vacuum at room temperature for 36 hours in the dark, to give 1.50 g [45.0% from the precursor phosphonium salt] of heteroarotinoic acid (38) as yellow needles: m.p 204°–204.5° C. dec; $^1$H NMR (DCCl$_3$) δ1.37 [s, 6H, (CH$_3$)$_2$C], 1.98 [m, 2H, ArSCH$_2$CH$_2$], 2.25 [s, 3 H, CH$_3$], 2.42 [s, 3 H, CH$_3$] 3.06 [m, 2 H, ArSCH$_2$CH$_2$], 5.86 [br s, 1 H, CH=CO$_2$H], 6.44 [d, 1H, J=15 Hz, CHC(CH$_3$) CHCO$_2$H], 6.59 [d, 1 H, J=12 Hz, ArC(CH$_3$)CH], 7.09 [d, 1 H, J=7 Hz, H(8)], 7.10 [dd, 1 H, J=12 Hz, J=15 Hz, CH—CH=CH], 7.21 [dd, 1 H, J=2 Hz, J=7 Hz, H(7)], 7.52 [d, 1 H, J=2 Hz, H(5)]; $^{13}$C NMR (DCCl$_3$) ppm 13.8 [CH$_3$], 16.1 [CH$_3$], 23.0 [ArSCH$_2$CH$_2$], 30.1 [(CH$_3$)$_2$C], 33.0 [(CH$_3$)$_2$C], 37.5 [ArSCH$_2$CH$_2$], 118.3[CHCO$_2$H], 123.3 [C(7)], 123.6 [C(5)] 125.4 [ArC(CH$_3$)CH], 126.4 [C(8)], 131.5, 131.7 [CH—CH=CH], 135.4 [CHC(CH$_3$) CHCO$_2$H], 138.1, 140.2, 141.7, 154.0 [C(CH$_3$)CHCO$_2$H], 170.8[CO$_2$H].

7-[4.4-Dimethylthiochroman-6-yl]-3,7-dimethyl-2,4,6-heptatrienoic acid (38)

Method 2

To a suspension of 3.56 g (0.0062 mol) of/phosphonium salt in ether/THF (50 mL 2:3 ether/THF) was added dropwise n-butyllithium in hexane (4.01 mL, 1.55 M., 0.1006 mol) at room temperature under N$_2$in a 100-mL, round bottom flask equipped with a condenser and nitrogen inlet. The resulting, dark orangish-red solution was cooled to −78° C. and 0.90 g (0.0062 mol) of ethyl (E)-B-formylcrotonate in 10 mL of ether was added dropwise in the dark. The solution was stirred for 10 minutes and warmed to −43° C.(10 min); a second equivalent of n-butyllithium (4.01 mL, 1.55M, 0.00621 mol) in hexane was added and the resulting orange solution was allowed to stir for 20 min. This solution was treated with 0.25 g (0.0686 mol) of HCl(g) in the THF followed by the addition of 0.69 g (0.093 mol) of t-butyl alcohol and 1.04 g (0.093 mol) potassium t-butoxide. The yellowish solution was allowed to warm to room temperature with stirring for 70 minutes; it was then diluted with 100 mL of hexane, filtered and evaporated (vacuum) to give a yellow oil. The resulting oil was added to a solution of 4.5 g (0.0802 mol) of KOH in aqueous ethanol (50 ml of 4:1 ethanol/H$_2$O) and the solution was boiled in the dark for 30 min. The reddish solution was cooled (RT), treated with 5.0 g of NaCl and extracted with 100 mL ether. The ether layer was extracted with water (4×50 mL), and the combined aqueous layers were acidified slowly with dilute H$_2$SO$_4$. At the neutralization point, solid began to form; the aqueous yellow suspension was extracted with ether (2×75 mL). The yellow ether layer was dried (Na$_2$SO$_4$) and evaporated (vacuum) to give a yellow solid. After fractional recrystallization (absolute ethanol), 0.88 g [43.1% from the precursor salt] of acid (38) was obtained as yellow needles with a mp of 204°–204.5° C. dec. $^1$H NMR (DCCl$_3$) δ1.37 [s, 6 H, (CH$_3$)$_2$C], 1.98 [m, 2 H, ArSCH$_2$CH$_2$], 2.25 [s, 3 H, CH$_3$], 2.42 [s, 3 H, CH$_3$]3.06 [m, 2 H, ArSCH$_2$CH$_2$], 5.86 [br s, 1 H, CH=CO$_2$H], 6.44 [d, 1 H, J=15 Hz, CHC(CH$_3$) CHCO$_2$H], 6.59 [d, 1 H, J=12 Hz, ArC(CH$_3$)CH], 7.09 [d, 1 H, J=7 Hz, H(8)], 7.10[dd, 1 H, J=12 Hz, J=2 Hz, H(5); $^{13}$C NMR (DDCl$_3$) ppm 13.8 [CH$_3$], 16.1 [CH$_3$)$_2$C], 23.0 [ArSCH$_2$CH$_2$], 30.1 [(CH$_3$)$_2$C], 33.0 [(CH$_3$)$_2$C], 37.5 [ArSCH$_2$CH$_2$], 118.3 [CHCO$_2$H], 123.3 [C(7)], 123.6[C(5)], 125.4 [ArC(CH$_3$)CH], 126.4 [C(8)], 131.5, 131.7 [CH—CH=CH], 135.4 [CHC(CH$_3$)CHCO$_2$H], 138.1, 140.2, 141.7, 154.0 [C(CH$_3$)CHCO$_2$H], 170.8 [CO$_2$H]. Anal. Calcd for C$_{20}$H$_{24}$O$_2$S: C, 73.13; H, 7.36; S, 9.76. Found: C, 73.31; H, 7.37; S, 10.01.

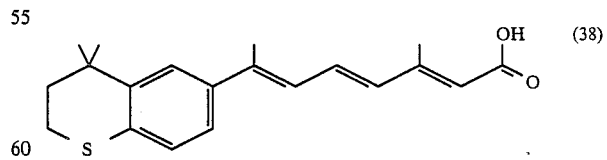

(38)

Ethyl 7-[4,4-Dimethylthiochroman-6-yl]-3,7-dimethyl-2,4,6-heptatrienoate (39)

To a suspension of 0.5030 g (0.00153 mol) of trans-heteroarotinoic acid (38) in 8 mL of dry ether was added 0.145 mL 0.0018 mol) of freshly distilled pyridine under $N_2$, and the mixture was cooled to $-10°$ C. in a 50-mL, round bottom flask equipped with a condenser and nitrogen inlet. A solution of 0.1005 g (0.123 mL, 0.00169 mol) of $SOCl_2$ in ether (1 mL) was added and stirring was continued at room temperature for 1 hour. The resulting dark red solution was filtered and cooled to $-20°$ C. Then 0.1420 g (0.145 mL, 0.00180 mol) of pyridine was added and 0.21 g (0.266 mL, 0.00459 mol) of dry ethanol was introduced all at once and stirring was maintained at room temperature for 3 hours. The yellow solution was diluted with 25 mL of ether and the new solution was washed with water (4×30 mL); the ether layer was dried ($Na_2SO_4$, 1 h). The solvent was removed (vacuum) and the resulting yellow oil was chromatographed on silica gel using hexane/ether (15:1) with the silica gel retaining the trans-heteroarotinoic acid (38). The ethyl ester (39) [0.4923 g, (88.1%)] was obtained as a viscous yellow oil; $^1H$ NMR ($DCCl_3$) $\delta 1.30$ [t, 3 H, $CO_2CH_2CH_3$], 1.36 [s, 6 H, $(CH_3)_2C$], 1.96 [m, 2 H, $ArSCH_2CH_2$], 2.22 [s, 3 H, $CH_3$], 2.38 [s, 3 H, $CH_3$], 3.14 [m, 2 H, $ArSCH_2 CH_2$], 4.19 [q, 2 H, $CO_2CH_2CH_3$], 5.82 [s, 1 H, CHCOOEt], 6.39 [d, 1 H, J=15 Hz, $CHC(CH_3)CHCO_2Et$], 6.55 [d, 1 H, J=12 Hz, $ArC(CH_3)CH$], 7.03 [dd, 1 H, J=12 H], 7.07 [d, 1 H, J=8 Hz, H(8)], 7.18 [dd, 1 H, J=2 Hz, J=8 Hz, H(7)], 7.48[d, 1 H, J=2 Hz, H(5)]; $^{13}C$ NMR ($DCCl_3$) ppm 13.8 [$CH_3$], 14.3 [$Ch_2Ch_3$]16.2[$CH_3$], 23.1 [$ArSCH_22CH_2$], 30.1 [$(CH_3)_2C$], 33.1 [$(CH_3)_2C$], 37.6 [$ArSCH_2CH_2$], 59.6 [$CH_2CH_3$], 118.7 [$CHCO_2Et$], 123.4 [C(7)], 123.6 [C(5)], 125.5 [CH—CH=CH], 126.4 [C(8)], 131.1 [CH—CH=CH], 135.5 [CH—CH=CH], 138.2, 139.9, 141.7, 152.3 [$C[CH_3]CHCO_2Et$], 167.1 [$CO_2Et$]. Anal Calcd for $C_{22}H_{28}O_2S$: C, 74.12; H, 7.92. Found: C, 74.35; H, 8.06.

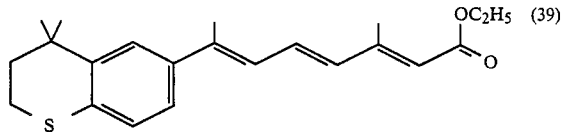

(2-Phthalimide-ethyl) 7-[4,4-Dimethylthiochroman-6-yl]-3-7-dimethyl-2,4,6-heptatrienoate (40)

To a suspension of 0.5030 g (0.00153 mol) of trans-heteroarotinoic acid 1b in 8 mL of dry ether was added 0.1420 g (0.184 mL, 0.00180 mol) of freshly distilled pyridine in a 50-mL, round-bottom flask equipped with a condenser and nitrogen inlet, and the suspension was cooled to $-10°$ C. A solution of 0.2005 g (0.123 mL, 0.00169 mol) of $SOCl_2$ in ether (1 mL) was added and the new solution was stirred at room temperature for 1 hour. The resulting dark red solution was filtered and cooled to $-20°$ C.; 0.1420 g (0.184 fmL, 0.00180 mol) of pyridine was added. Then 0.2963 g (0.00155 mol) of N-2-hydroyethylphthalimide in 8 mL of dry DMF was introduced at room temperature and the solution was allowed to stir for 10 hours. The resultant yellow solution was diluted with ether (25 mL) and washed with water (5×60 mL); and the ether layer was dried ($Na_2SO_4$, overnight). The solvent was removed (vacuum) and the resulting yellow solid was chromatographed on silica gel using $DCCl_3$. The phthalimide-substituted heteroarotinoid (40) [0.2731 g (35.6%)] was a yellow solid: mp 64°-65° C.; IR (KBr) 1760-1710 cm—1;$^1H$ NMR ($DCCl_3$) $\delta 1.36$ [s, 6 H, $(CH_3)_2C$], 1.98 [m, 2 H, $ArSCH_2CSH_2$], 2.24 [s, 3 H, $CH_3$], 2.34 [s, 3 H, $CH_3$], 3.06 [m, 2 H, $ArSCH_2CH_2$], 4.03 [t, 2 H, $CO_2CH_2CH_2$], 4.40 [t, 2 H, $CO_2CH_2CH_2$], 5.78 [s, 1 H, $CHCO_2CH_2CH_2$], 6.38 [d, 1 H, J=15 Hz, $CHC(CH_3CHCO_2CH_2]$, 6.55 [d, 1 H, J=12 Hz, $ArC(CH_3)CH$], 7.03 [dd, 1 H, J=12 Hz, J=15 Hz, CH—CH=CH], 7.08 [d, 1 H, J=8 Hz, H(8)], 7.18 [dd, J=2 Hz, J=8 Hz, H(7)], 7.48 [d, H, J=2 Hz, H(5)], 7.75 [m, 2 H], 7.80 [m, 2 H]; $^{13}C$ NMR ($DCCL_3$) ppm 13.9 [$CH_3$], 16.2 [$CH_3$], 23.1 [$ArSCH_2CH_2$], 30.2 [$(CH_3)_2C$], 33.1 [$(CH_3)_2C$], 37.1 [$CO_2CH_2CH_2$], 37.6 [$ArSCH_2CH_2$], 60.8 [$CO_2CH_2CH_2$], 117.9 [$CHCO_2CH_2CH_2$], 123.3 123.4 [C(7)], 123.6 [C(5)], 125.5 [CH—CH=CH], 126.5 [C(8)], 131.4, 131.8, 132.0 [CH—CH=CH], 134.0, 135.4 (CH—CH=CH], 138.2 140.1, 141.8, 153.5 [$C(CH_3)CHCO_2CH_2$], 166.6 [$CO_2CH_2CH_2$], 168.0 [$CH_2N(C=O)_2$]; Anal. Calcd for $C_{30}H_{31}NO_4S$: C, 71.83; H, 6.23; N, 2.79. Found C, 71.47; H, 6.31; N, 2.76.

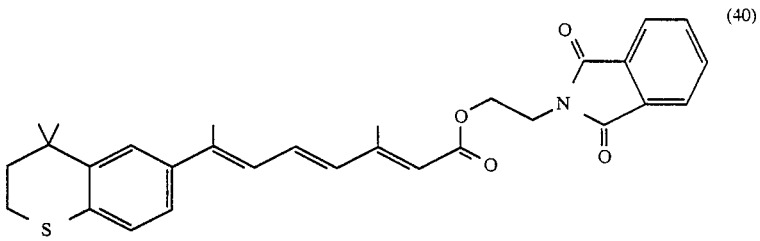

2-(2-Methoxy-5-bromophenyl)-2-methyl-1-chloropropane (41)

Concentrated $H_2SO_4$ (4 mL, 7.6 g, 0.077 mol) was added dropwise under $N_2$ to stirred 4-bromoanisole (44.0 g, 0.235 mol). After warming the mixture to 36° C. (warm water bath), distilled $\beta$-methallyl chloride (21.5 mL, 20.0 g, 0.221 mol) was added dropwise to the stirred mixture in 4 equal portions over a period of 1.6 hours (4×0.4 h). During the addition of the $\beta$-methallyl chloride, the temperature of the mixture was maintained at 35°-44° C. (using a warm water bath). After the addition of the $\beta$-methallyl chloride was complete (1.6 h), the reaction mixture became solid and was allowed to stand [1 hour over water bath (29°-32° C.), 2 hours at room temperature]. The wet solid was partitioned between $H_2CCl_2$ (500 mL) and $H_2O$ (175 mL). The organic layer was separated and then washed with 5% aqueous $NaHCO_3$(175 mL) and $H_2O$ [175 mL, 5 mL of brine being added to destroy an emulsion which formed]. After drying ($MgSO_4$, 36 h), the organic solution, the solvent was removed, and the solid residue was vacuum distilled to remove a lower boiling liquid (bp 42° C./0.15 mm-95° C./0.07 mm, mostly 4-bromoanisole). A solution of the remaining solid residue in $H_2CCl_2$ was treated with decolorizing charcoal.

Evaporation of the H₂CCl₂ gave a tan solid which was recrystallized (twice, heptane) and dried [traces of solvent were removed (high vacuum)] to give the aryl ether as a white crystalline solid (37.7 g, 61.5%); mp 87.8°–89.1° C. [literature reports 82°–84° C.; see P. Gates, D. Baldwin, C. A. Wilson and J. Gillion (Fison's Ltd.), U.S. Pat. No. 4,333,759; Chem Abstr. 1982, 97, 215978 p]. Another 3.4 g (5.5%) could be obtained by the following procedure. Evaporation of the mother liquors gave a solid which was dissolved in H₂CCl₂. Partial decolorization (charcoal) of the H₂CCl₂ solution followed by evaporation gave a solid residue which was recrystallized (twice, heptane); the yield of ether was 41.1 grams (67%). IR(KBr) 1246 cm⁻¹(C—O); ¹H NMR (DCCl₃) δ1.43 [s, 6 H, C (CH₃)₂], 3.84 (s, 3 H OCH₃), 3.96 (s, 2 H, OCH₂), 6.78 (d, 1 H, Ar-H), 7.32–7.41 (m, 2 H, Ar-H); ¹³C NMR (DCCl₃) ppm 25.8 [C(CH₃)₂], 40.4 [C(CH₃)₂], 53.3 [CH₂Cl], 55.3 [OCH₃]; Ar-C[113.1, 130.6, 131.2, 135.4, 157.2] Both hydrogen and carbon-13 NMR spectral shifts were measured from tetramethylsilane (TMS) on a Varian XL-300 NMR spectrometer confirming the correct hydrogen distribution and carbon atoms assignments.

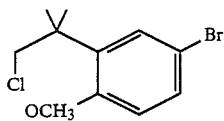

(41)

5-Bromo-2,3-dihydro-3,3-dimethylbenzofuran (42)

A mixture of 2-(2-methoxy-5-bromophenyl)-2-methyl-1-chloropropane (ether above; 12.60 g 0.045 mol), pyridine hydrochloride (23.7 g 0.205 mol), and quinoline (22.9 g 0.177 mol) was heated to 164° C. (boiling isobutylbenzene bath) under N₂ with stirring over a period of 0.6 hours. After stirring at reflux (164°–167° C.) for 3 hours, the mixture was partitioned between ice-cold 6 N HCl (225 mL). The organic layer was separated and the aqueous layer was extracted (ether 200 mL). After drying (MgSO₄, overnight) the combined organics, the solvent was evaporated and the residual oil was vacuum distilled to give the cyclic ether (8.5 g, 82%) as a colorless liquid: bp 48.2°–60.0° C./0.05–0.06 mm [literature reports 62°–64° C./0.01 mm; see P Gates, D. Baldwin, C. A. Wilson and J. Gillion (Fison's Ltd.), U.S. Pat. No. 4,333,759;Chem. Abstr. 1982, 97, 215978 p)]. TLC analysis [1:5 ethyl acetate:petroleum ether (bp 50°–110° C.)] indicated traces of two impurities. IR(neat) 1197 cm⁻¹ (C—O); ¹H NMR (DCCl₃) δ1.31 [2,6 H, C(CH₃)₃)₂], 4.24 (s, 2 H, OCH₂), 6.67 (d, 1 H, Ar-H), 7.18–7.25 (m, 2 H, Ar-H); ¹³C NMR (DCCl₃) ppm 27.3 [C(CH₃)₂] 84.7 [OCH₂]; Ar-C [111.2, 112.2, 125.4, 130.6, 138.9 158.2].

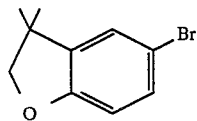

(42)

1-(2,3-Dihydro-3,3-dimethyl-5-benzofuranyl) ethanol (43)

A mixture of the precursor ether (0.21 g 0.9 mmol), Mg turnings (1.0 g 0.041 g at) and dry THF (2 mL) was heated (heat gun) under N₂ until the mixture turned cloudy (ca 15 min). Dry THF (15 mL) was added to the mixture which was then heated to reflux. A solution of ether (42) (2.92 g, 12.9 mmol) in dry THF (25 mL) was added dropwise to the vigorously stirred mixture over a period of 0.75 hours. After vigorous stirring at reflux for 2.75 hours, another 0.25 g (0.010 g at) of Mg turnings were added. The new mixture was stirred at reflux for 0.75 hour and with no external heat for 0.5 hours. Upon cooling the mixture to −5° to −10° C. (ice-salt bath), a solution of freshly distilled acetaldehyde (2.0 g, 0.045 mol) in dry THF (20 mL) was added dropwise to the vigorously stirred mixture over a period of 0.7 hours. This reaction mixture was stirred in an ice-salt bath (−5° to −10° C.), for 1.5 hours, after which time a solution of acetaldehyde (0.9 g, 0.020 mol) in dry THF (5 mL) was added dropwise (over a period of about 0.2 h) and the new mixture was stirred 0.3 hours. With continued cooling (−5° to −10° C.), saturated aqueous NH₄Cl (3 mL) was added and the excess Mg turnings were removed by filtration. Saturated aqueous NH₄Cl (10 mL) and ether rinses (of glassware and Mg turnings, 60 mL) were added to the filtrate. After separating the organic layer, the aqueous phase (pH≧8) was acidified (pH 6.5 to 7) with saturated aqueous NH₄Cl (15 mL) and 4% H₂SO₄ (14 mL). The aqueous solution was extracted with ether (5 ×40 mL) and ether (90 mL) was added to the combined organics. The organic solution was washed with saturated aqueous NaHCO₃ (75 mL) and brine (50 mL). After drying (MgSO₄) the solution, the solvent was removed, and the residual oil was chromatographed through a circular silica gel plate (4 mm) spun by a Chromatotron (Model 7924T, Harrison Research, 840 Moana Court, Palo Alto, Calif.). Half of the product was eluted with ether/petroleum ether (bp 50°–110° C.) 20:1, 8:1, and 4:1 and then the same solvent system was used to elute the other half. In both separations, the 4:1 ratio was required to elute the title compound. Concentration of the eluent in the desired fractions gave 1.18 g (44%) of the alcohol as a light yellow, viscous oil. TLC analysis (1:4 ether:petroleum ether, bp 50°–110° C.) indicated the compound was essentially pure.

IR (neat) 3150–3650 cm⁻¹; ¹H NMR (DCCl₃) δ1.31 [s, 3 H, C(CH₃)CH₃], 1.32 [s, 3 H, C(CH₃)CH₃], 1.45 [d, 3 H, CH(CH₃)], 2.36 (bs, 1 H, O-H), 4.81 [q, 1 H, CH(CH₃)], 6.71 [d, J=8 Hz, 1 H, H(7)], 7.08 [dd, J=1.9 Hz, 1 H, H(6)], 7.13 [d, J=1.9 Hz, 1 H, H(4)]; ¹³C NMR (DCCl₃) ppm 25.1 [CH(CH₃)], 27.5 [C(CH₃)₂], 41.9 [C(CH₃)₂, 7.02 [C-OH], 84.7 [OCH₂]; Ar-C [109.3, 119.5, 125.4, 136.8, 138.3, 158.6].

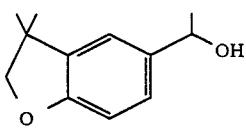

(43)

[1-(2,3-Dihydro-3,3-dimethyl-5-benzofuranyl) ethyl] triphenylphosphonium Bromide (44)

A solution of the precursor alcohol (43) (0.28 g, 1.46 mmol) in methanol (5 mL) was added dropwise (about 3 min.) under N₂ to a stirred mixture of triphenylphosphine hydrobromide (0.50 g, 1.46 mmol) in methanol (10 mL). After 7 minutes, the mixture became a solution which was stirred at room temperature for 40 hours.

Evaporation of the solvent resulted in foaming and gave a colorless solid. The solid was changed to a powder by stirring the suspension of crude (44) in ether for 4.5 hours. After filtering the solid, the fine powder was partially dried (air) and finally dried by high vacuum (P$_2$O$_5$, 100° C.), to give 0.69 g (88%) of the phosphonium salt as a creamy white powder; mp 207°-212° C.; $^1$H NMR (DCCl$_3$) δ1.14 [s, 3 H, (CH$_3$)CCH$_3$], 1.19 [s, 3 H, (CH$_3$)CCH$_3$], 1.82 (dd, 3 H, CHCH$_3$), 4.22 (s, 2 H, OCH$_2$), 6.56 (m, 1 H, CHCH$_3$), 6.61 (d, 1 H, Ar-H), 6.85–6.98 (m, 2 H, Ar-H), 7.64–7.92 [m, 15 H, P(C$_6$H$_5$)$_3$]. The salt was used without further purification.

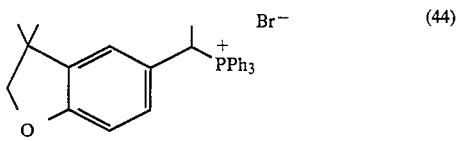

6-[(3-Triphenylphosphonyl)-1-methyl-1-propenyl]-4,4-dimethylchroman (45)

A solution of 4,4-dimethylchroman-6-yl methyl ketone (5.44 g, 26.67 mmol) in dry ether (20 mL) was added dropwise under N$_2$ to a stirred solution of vinylmagnesium bromide in THF (40 mL, 40 mmol). The mixture was allowed to react for 3.5 hours and was then quenched with saturated, aqueous NH$_4$Cl solution with cooling. The supernatant liquid was decanted and the residue was washed (dry ether, 100×3). The combined organic washings were dried (Na$_2$SO$_4$) and then the solvent was evaporated in vacuo to five 7.07 g of crude vinyl alcohol shown below. This crude alcohol

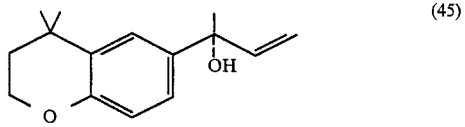

(7.07 g, 30.4 mmol) was dissolved in 30 mL of CH$_3$OH and the solution was added to a cold solution of triphenylphosphine hydrobromide (10.45 g, 30.47 mmol) in CH$_3$OH (30 mL). The resulting solution was kept at room temperature with stirring for 2.5 hours. When the solution was poured slowly into dry ether (550 mL), a precipitate formed and was filtered off and dried for 2 hours under vacuum at room temp. The yield of the salt shown below was 9.14 g (61.5%); mp 261°-262° C.; IR (KBr) 2975 (C-H), 1667 (C=C) cm$^{-1}$; $^1$H NMR (DCCl$_3$) δ1.29 [s, 6 H, CH$_3$ (9,10)], 1.76–1.84 [m, 2 H, H(3)], 4.14–4.20 [m, 2 H, H(2)], 4.75–4.83 [dd, 2 H, H(12)], 5.54 [m, 1 H, H(11)], 6.68–6.71 [d, 1 H, H(7)], 6.88–6.91 [s, 1 H, H(5)], 7.07 [s, 1 H, H(5)], 7.60–8.00 [m, 15 H, Ar-H]. The salt was used without further purification. Other runs have given yields as high as 82%.

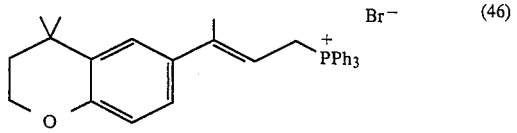

7-[4,4-Dimethylchroman-6-yl]-3,7-dimethyl-2,4,6-heptatrienoic acid (47)

A solution of n-butyllithium (8.20 mL, 1.31M, 10.77 mmol) in hexane was added dropwise under argon to a stirred suspension of the precursor phosphonium salt (5.99 g, 10.77 mmol) in dry ether (100 mL). The resulting dark reddish-brown mixture was stirred at room temp for 10 minutes. To this mixture was added a solution of ethyl 3-formyl-2-butenoate (1.54 g, 10.77 mmol) in dry ether (30 mL). After stirring for 2 hours at room temp, the mixture was filtered and the resultant solid was washed (ether 250 mL). The combined filtrates were then concentrated in vacuo to yield 2.40 g (68.4%) of crude ester. This ethyl ester was then subjected to chromatography over silica gel using ethyl acetate:petroleum ether (2%:98%). The middle fraction of ester (70 mg) was then saponified using KOH (1.20 g, 21.4 mmol) in water (2 mL) and ethanol (80 mL). The procedure involved protecting the mixture from light while it was stirred at 50° C. for 4 hours under N$_2$. After cooling to 0° C., the final mixture was acidified with 6 N HCl and the resulting mixture was extracted (HCCl$_3$, 2×25 mL). The extracts were washed with brine solution, dried (Na$_2$SO$_4$, 15 min) and then evaporated. Yellow crystals of acid (47) were obtained and then were recrystallized (abs ethanol) to yield a final weight of 29 mg (45.3%); mp 218°-218.5° C. IR (KBr) 3250-2500 cm$^{-1}$ (O-H), 1680 (C=O) cm$^{-1}$; $^1$H NMR (DCCl$_3$) δ1.35 [s, 6 H, (CH$_3$)$_2$], 1.79–1.83 [t, 2 H, H(3)], 2.20 [3 H, CH$_3$ (12)], 2.32 [s, 3 H, CH$_3$ (17)], 4.15–4.18 [t, 2 H, H(2)], 5.76 [s, 1 H, H(18)], 6.40–6.45 [d, 1 H, H(15)], 6.53–6.57 [d, 1 H, H(13)], 6.68–6.71 [d, 1 H, H(8)], 6.96–7.05 [dd, 1 H, H(14)], 7.19–7.23 [dd, 1 H, H(7)], 7.41–7.42 [d, 1 H, H(5)]; $^{13}$C NMR ppm 13.43 [C(17)], 16.0 [C(12)], 30.3 [C(4)], 30.8 [C(CH$_3$)$_2$], 38.87 [C(3)], 62.57 [C(2)], 115.5 [C(8)], 116.5 [C(18)], 123.5 [C(5)], 124.3 [C(7)], 131.1 [C(13)], 133.9 [C(14)], 135.1 [C(6)], 151.1 [C(8a)], and 167.9 [C(19)]. Other signals not assigned appeared at: 119.2, 139.1, 151.5, and 153.2 ppm. Anal. Calcd for C$_{20}$H$_{24}$O$_3$: C, 76.89; H, 7.74. Found: C, 76.79; H, 7.90.

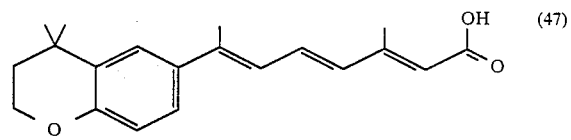

4,4-Dimethylchroman or 3,4-Dihydro-4,4-dimethyl-2H-1-benzopyran (48)

A solution of 2-methyl-4-phenoxy 2-butanol (41.10 g, 288.33 mmol) in freshly distilled nitromethane (40 mL) was added dropwise under N$_2$ to a stirred suspension of anhydrous AlCl$_3$ (41.43 g, 308.1. mmol) in freshly distilled nitromethane (165 mL). After stirring at room temperature for an additional 24 hours, a solution of 6M HCl (425 mL) was added slowly. The resulting mixture was stirred for 10 minutes and diluted with ether (200 mL). The layers were separated, and the organic layer was washed with H$_2$O (200 mL), saturated NaHCO$_3$ (4×150 mL), H$_2$O (150 mL), and saturated solution of NaCl (2×150 mL). After the solution was dried (MgSO$_4$, 30 min), the solvent was removed (vacuum). Vacuum distillation of resulting dark brown oil gave 27.96 rams (75.6%) of the pyran (48) as a colorless liquid: bp 43°–44° C./0.2 mm [literature reports 93° C./10 mm; see J. Colonge, E. Le Sech, and R. Marey *Bull. So. Chim. France*, 776 (1957)]; $^1$H NMR (DCCl$_3$) δ1.27 [s, 6 H, (CH$_3$)C], 1.83 [m, 2 H, CH$_2$], 4.09 [m, 2H, OCH$_2$], 6.88–7.24 [m, 4 H, Ar-H]; $^{13}$C NMR (DCCl$_3$) ppm 30.5 [C(CH$_3$)$_2$], 31.1 [(CH$_3$)$_2$C], 37.7 [CH$_2$], 63.0 [OCH$_2$], Ar-C [116.9, 120.4, 126.9, 127.0, 131.6, 153.6].

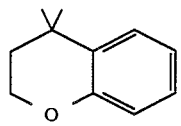

(48)

4,4-Dimethylchroman-6-yl Methyl Ketone or 1-(3,4-Dihydro-4,4-dimethyl-2H-1-benzopyran-6-yl)ethanone (49)

Anhydrous AlCl$_3$ (2.99 g, 22.51 mmol) was added in small portions to 4,4-dimethylchroman (3.45 g, 21.30 mmol) and acetyl chloride (1.51 mL, 21.30 mmol) in CH$_3$NO$_2$ (30 mL) under N$_2$. After stirring at room temperature for 6 hours, 6M HCl (30 mL) was added slowly, and the resulting mixture was stirred for 10 minutes. The mixture was diluted with ether (70 mL) and the layers were separated. The organic layer was washed with H$_2$O (50 mL), saturated aqueous NaHCO$_3$ (4×40 mL), H$_2$O (50 mL), and saturated solution of NaCl (50 mL). After the solution was dried (MgSO$_4$, 30 min), the solvent was removed to leave a dark, reddish brown oil. Vacuum distillation gave 3.09 g (89.03%) of the ketone as a pale yellow liquid: bp 94°–95° C./0.1 mm [literature reports 108°–112° C./0.01 mm; see K. M. Waugh, K. D. Berlin, W. T. Ford, E. M. Holt, J. P. Carrol, P. R. Schomber, M. D. Thompson, and L. J. Schiff *J. Med. Chem.*, 28, 116 (1985)]; IR (neat) 1675–1685 cm$^{-1}$ (C=O); $^1$H NMR (DCCl$_3$) δ1.38 [s, 6 H, (CH$_3$)$_2$C], 1.84 [m, 2 H, CH$_2$], 2.52 [s, 3 H, CH$_3$C], 4.26 [m, 2 H, CH$_2$O], 6.82 [d, 1 H, H(8)], 7.71 [dd, 1 H, H(7)], 7.99 [d, 1 H, H(5)]; $^{13}$C NMR (DCCl$_3$) ppm 26.1 [CH$_3$], 30.5 [C(CH$_3$)$_2$], 30.6 [(CH$_3$)$_2$C], 37.0 [CH$_2$], 63.3 [CH$_2$O], 116.7 [C(8)], 127.5 [C(5)], 127.9 [C(7)], 130.0, 131.6 [C(4a), C(6), 157.8 [C(8a)], 196.4 [C=O]. Mass spectral data for C$_{13}$H$_{18}$O$_2$: m/e(M$^-$) 204.1150; Found: 204.1155.

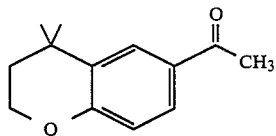

(49)

α,4,4-Trimethylchroman-6-methanol or 3,4-Dihydro-4,4-trimethyl-2H-1-benzopyran-6-methanol (50)

A solution of the methyl ketone (49) (180 g, 88.1 mmol) in anhydrous ether (80 mL) was added dropwise under N$_2$ to a stirred suspension of LiAlH$_4$ (5.01 g, 132.27 mmol) in dry ether (315 mL). The mixture was heated at reflux for 24 hours. After cooling to room temperature, ethyl acetate (85ml) was added dropwise to destroy the excess LiAlH$_4$. A solution of 5% HCl (255 mL) was then added, and the resulting mixture was stirred for 5 minutes. The layers were separated, and the aqueous layer was washed (ether 3×150 mL). The combined organic layers were washed with 5% aqueous Na$_2$CO$_3$ (2×100 mL) and water (150 mL) followed by a saturated NaCl solution (150 mL). After the solution was dried (MgSO$_4$, 30 min.) the solvent was removed leaving a yellow oil which solidified after scratching. Recrystallization (hexane) gave 15.25 grams (82.9%) of the alcohol (50) as a white solid: mp 71°–72° C. [literature reports 70°–71° C.; see K. M. Waugh, K. D. Berlin, W. T. Ford, E. M. Holt, J. P. Carrol, P. R. Schomber, M. D. Thompson, and L. J. Schiff *J. Med. Chem.* 28, 116 (1985)]; IR (KBr) 3140–3640 cm$^{-1}$ (OH); $^1$H NMR (DCCl$_3$) δ1.32 [s, 6 H, (CH$_3$)$_2$C], 1.50 [d, 3 H, CH$_3$], 1.31 [s, 1 H, OH], 4.20 [m, 2 H, H(2)], 4.84 [q, 1 H, CHOH], 6.76 [d, 1 H, H(8)], 7.07 [dd, 1 H, H(7)], 7.28 [d, 1 H, H(5)]; $^{13}$C NMR (DCCl$_3$) ppm 24.9 [CH$_3$], 30.6 [C(4)], 31.0 [(CH$_3$)$_2$C], 37.6 [C(3)], 62.9 [C(2)], 70.2 [C(9)], 116.8 [C(8)], 123.9, 124.2 [C(5), C(7)], 131.1, 137.6 [C(4a), C(6)], 152.9 [C(8a)].

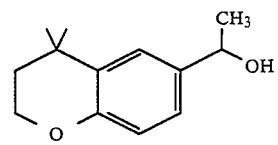

(50)

[1-4,4-Dimethylchroman-6-yl)ethyl]triphenylphosphonium Bromide or [1-(3,4-Dihydro-4,4-dimethyl-2H-1-benzopyran-6-yl)ethyl]triphenylphosphonium Bromide (51)

A solution of the alcohol precursor (50) (0.70 g, 3.4 mmol) and triphenylphosphine hydrobromide (1.2 g, 3.5 mmol) in methanol (30 mL) was stirred under N$_2$ at room temperature for 24 hours. The solvent was removed (vacuum), and the resulting oil was triturated repeatedly with dry ether until it solidified. The white solid was suspended and stirred in dry ether (30 mL) at room temperature under N$_2$ for 4 hours, filtered, and dried (110° C./2 mm) to give 1.75 g (96.9%) of the salt as a white powder: mp 152°–156° C. (dec) [literature reports 149°–155° C.; see K. M. Waugh, K. D. Berlin, W. T. Ford, E. M. Holt, J. P. Carrol, P. R. Schomber, M. D. Thompson, and L. J. Schiff *J. Med. Chem*, 28, 116 (1985)]; $^1$H NMR (DCCl$_3$) δ1.08 [s, 3 H, CH$_3$], 1.14 [s, 3 H, CH$_3$], 1.76 [m, 2 H, H(3)], 1.83 [d, 3 H, CHCH$_3$], 4.16 [m, 2 H, H(2)], 6.3 [m, 1 H, CH$^+$PPh$_3$, Br$^-$], 6.57 [d, 1 H, H(8)], 6.67 [d, 1 H, H(7)], 7.74 [brs, 1 H, H(5)], 7.63–7.84 [m, 15 H, $^+$P(C$_6$H$_5$)$_3$]. The salt was used without further purification.

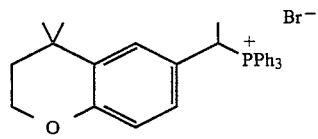

(51)

(E)-1-(5-Acetoxymethyl-2-furanyl)-2-(3,4-dihydro-4,4-dimethyl-2H-1-benzopyran-6-yl)propene (52)

A solution of n-butyllithium in hexane (1.55M, 1.23 mL, 1.88 mmol) was added dropwise under N$_2$ to a stirred suspension of the precursor phosphonium salt 51 (1 g, 1.88 mmol) in dry ether (20 mL). The resulting solution was cooled to −78° C., and a solution of 5-acetoxymethyl-2-furanaldehyde (0.316 g, 1.88 mmol) was added over a period of 1 minute. The solution was stirred for a few minutes at −78° C. and then at room temperature for 24 hours. The mixture changed from reddish-brown to a pale brown color. After 24 hours, the reaction mixture was filtered. The resulting solid was washed with 45 mL of ether (anhydrous), and the filtrate was concentrated to give a yellow oil. This yellow oil was refrigerated for 24 hours and became a dark yellow solid. This solid was passed through 20 grams of silica gel [column, (8×200 MM)]. The product was eluted with 300 mL of hexane:ethyl acetate (4:1) concentration of eluent gave a viscous oil from which yellow solid was obtained after keeping it in ice bath at 0° C. for 5 hours. Recrystallization (hexane) gave 0.12 grams (19%) of the ester (52) as a white crystaline solid: mp 80°–81° C. $^1$H NMR (DCCl$_3$) δ1.37 [s, 6 H, H(9), H(10)], 1.85 [m, 2 H, H(3)], 2.1 [s, 3 H, H(20)], 2.36 [s, 3 H, H(12)], 4.20 [m, 2 H, H(2)], 5.08 [s, 2 H, H(18)], 6.31 [d, 1 H, J=3 Hz H(16)], 6.46 [d, 1 H, J=3 Hz H(5)], 6.53 [s, 1 H, H(13)], 6.77 [d, 1 H, J=9 Hz, J=3 Hz H(8)], 7.21 [dd, 1 H, H(7)], 7.39 [d, 1 H, H(15)]; $^{13}$C NMR (DCCl$_3$) ppm 18.24 [C(12)], 20.94 [C(20)], 30.69 [C(4)], 31.06 [C(9), C(10)], 37.63 [C(3)], 58.31 [C(18)], 63.11 [C(2)], 109.54 [C(16)], 114.15 [C(15)], 116.8 [C(8)], 124.36 [C(5)], 124.77 [C(7)], 70.69 [C(19)], nonprotonated and vinylic carbons [131.3, 135.6, 136.9, 147.7, 153.3, 154.6]. Mass spectral data for $C_{21}H_{24}O_4$: m/e (M$^-$) 340.1674. Found: 340.1679. Anal. calcd. for $C_{21}H_{24}O_4$: C, 74.08; H, 7.06. Found: C, 73.88; H, 7.09.

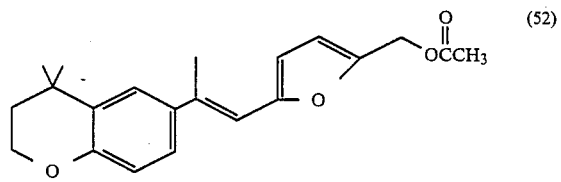

(52)

In order to demonstrate and evaluate the biological activity of the heteroarotinoids according to the present invention, selected compounds were assayed either via analysis of the suppression of the 12-o-tetradeconoyl-phorbol-13-acetate (TPA) induced synthesis of ornithine decarboxylase (ODC) in mouse skin or the induction of differentiation of human (HL-60) promyelocytic cells. In the ODC assay, either 13-cis-retinoic acid or trans-retinoic acid was employed. The following Table summarizes the result of the ODC assays.

TABLE

| Heteroarotinoids Test System | Dose, nmol | Retinoid ODC Activity | % of Inhibition as Compared to Control |
|---|---|---|---|
| Acetone | 0.0 | 0.00 ± 0.0* | — |
| Acetone + TPA[1] | 0.0 | 0.90 ± 0.31* | control |
| 13-cis-retinoic acid + TPA | 17 | 0.1 ± 0.01* | 89% |
| (38) + TPA | 17 | 0.1 ± 0.01* | 89 |
| (39) + TPA | 17 | 0.0 ± 0.0* | 100 |
| Acetone | 0.0 | 0.00 ± 0.0** | — |
| Acetone + TPA | 0.0 | 1.67 ± 0.14** | Control |
| 13-cis-retinoic acid + TPA | 17 | 0.14 ± 0.04** | 92 |
| (40) + TPA | 34 | 0.97 ± 0.13** | 42 |

TABLE-continued

| Heteroarotinoids Test System | Dose, nmol | Retinoid ODC Activity | % of Inhibition as Compared to Control |
|---|---|---|---|
| (47) + TPA | 34 | 1.4 ± 0.2** | 74 |

*nmol CO$_2$/30 min/mg protein
**nmol CO$_2$/60 min/mg protein $^1$TPA = 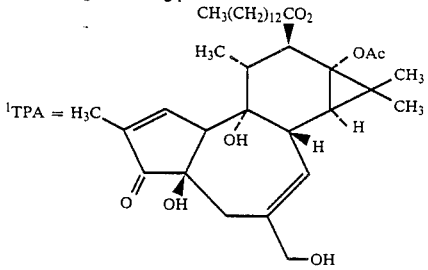

In the screening tests of the Table, the selected retinoids in 0.2 ml of acetone were applied 1 hour before the application of 10 nmole of TPA to the shaved backs of mice; the mice were then sacrificed for ODC assay 5 hours after TPA treatment. Epidermus was separated, homogenized, and centrifuged at 30,000×g. Soluble epidermal ODC activity was assayed. The retinoids were evaluated in three independent experiments (3 groups of mice with 3 mice per group) and the results from the experiments were normalized (% inhibition) for comparison. As seen from the data, the ethyl ester of the thiochromanyl structure (39) had the strongest activity. In comparison with 13-cis-retinoic acid as the standard, the ester (39) was more active while the acid form (38) was essentially equivalent in activity to the standard. In the experiments with trans-retinoic acid as the standard, the acid form of the chromanyl structure (47) was slightly less active than the standard. The related ester (40) with the large polar group was less active compared to the same control. Which standard is used appears to be relatively unimportant for determining activity in the assay, but the data presented in the Table identifies the standard for the sake of clarity and accuracy of presentation. Thus, the presence of the heteroatom in these arotinoids has not eliminated biological activity. It is also clear that the acid in the simple esters are the most active regardless of whether sulfur oxygen is the heteroatom. Consequently, the nature of the terminus group is also important.

In order to evaluate the efficacy of the heteroarotinoids to induce HL-60 cell differentiation along the granulocytic maturation pathway, human HL-60 cells were grown in a serum-free medium consisting of HRPMI 1640 supplemented with 10 nM 4-(2-hydroxyethyl)-1-piperazineethane sulfonic acid, 5 ug of insulin/mL, and 5 ug of transferrin/mL. These mature cells, unlike the uninduced HL-60, produced superoxide anion when simulated with an appropriate agent, such as TPA. The ability of the individual cells to produce superoxide can be measured by incubating cells with the water-soluble yellow dye, nitroblue tetrazolium (NBT). NBT is reduced to a water-insoluble blue-black formazan by superoxide. This formazan precipitate is associated with those cells that produce superoxide. Thus, the percentage of cells in a population that produce superoxide (NBT-positive cells) can be enumerated under a light microscope.

The retinoids were dissolved in DMSO or ethanol and diluted into the culture medium so that the final concentration of the solvent did not exceed 0.1%, a concentration that has no effect on differentiation. After incubation for 4 days at 37° C. in a humidified atmosphere of 5% CO₂ and air, the capacity of the cells to reduce NBT was determined. Viable cells (10⁶) were harvested by centrifugation and suspended in 0.5 mL of RPMI 1640 containing 20% fetal bovine serum. This cell suspension was mixed with an equal volume of phosphate buffered saline containing 1 mg of NBT/mL and 200 mg of TPA/mL. The reaction mixture was incubated at 37° C. for 25 minutes, and the reaction was terminated by cooling in an ice water bath. Cytospin slides were prepared from a portion of this reaction mixture and stained with Wright-Giemsa. A minimum of 200 cells were counted under light microscopy to determine the percentage of cells with cell-associated formazan.

The dose-response of HL-60 to trans-retinoic acid, the thiochromanyl acid (38) and the chromanyl acid (47) is shown in FIG. 1. The concentration of retinoid effective in achieving a half-maximal response (ED₅₀) is 41 nM for trans-retinoic acid, 72 nM for (38), and 200 nM for (47). Based on the above observed relative activities, it appears as if the oxygen-substituted derivatives are of a slightly less activity than the sulfur-substituted derivatives.

Having thus described and exemplified the preferred embodiments with a certain degree of particularity, it is manifest that many changes can be made within the details of operation, operating parameters, and steps for synthesizing and using the heteroarotinoids according to the present invention without departing from the spirit and scope of this invention. Therefore, it is to be understood that the invention is not limited to the embodiments set forth herein for purposes of exemplification, but is to be limited only by the scope of the attached claims, including the full range of equivalents to which each step thereof is entitled.

We claim:

1. A heteroarotinoid characterized by the formulae:

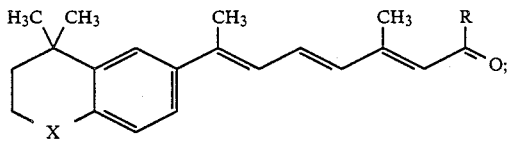

or

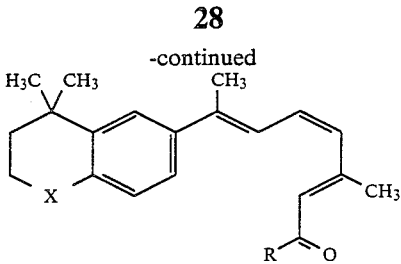

where X is S or O; and R is —H, —OH, —OC₂H₅ or

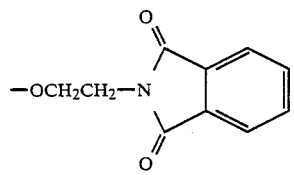

2. A heteroarotinoid of claim 1 where X is S and R is —H.

3. A heteroarotinoid of claim 1 where X is S and R is —OH.

4. A heteroarotinoid of claim 1 where X is S and R is —OC₂H₅.

5. A heteroarotinoid of claim 1 where X is S and R is

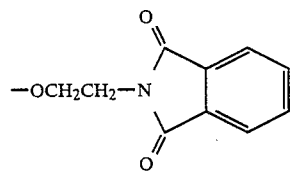

6. A heteroarotinoid of claim 1 where X is O and R is —H.

7. A heteroarotinoid of claim 1 where X is O and R is —OH.

8. A heteroarotinoid of claim 1 where X is O and R is —OC₂H₅.

9. A heteroarotinoid of claim 1 where X is O and R is

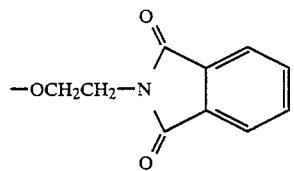

* * * * *